United States Patent [19]
Gustafsson et al.

[11] Patent Number: 4,636,501
[45] Date of Patent: Jan. 13, 1987

[54] PARA-SUBSTITUTED 3-PHENOXY-1-CARBONYLAMINO-ALKYLAMINO-PROPANOL COMPOUNDS, BETA RECEPTOR BLOCKING COMPOSITIONS AND USE

[75] Inventors: Bill B. R. Gustafsson, Bollebygd; Sven A. Hedberg, Gråbo; Bo T. Lundgren, Frillesås, all of Sweden

[73] Assignee: Aktiebolaget Hassle, Molndal, Sweden

[21] Appl. No.: 757,763

[22] Filed: Jul. 22, 1985

Related U.S. Application Data

[63] Continuation of Ser. No. 621,147, Jun. 18, 1984, abandoned, which is a continuation of Ser. No. 482,266, Apr. 5, 1983, abandoned, which is a continuation-in-part of Ser. No. 450,006, Dec. 15, 1982, abandoned.

[30] Foreign Application Priority Data

Dec. 17, 1981 [SE] Sweden .................. 8107574

[51] Int. Cl.$^1$ .................. A61K 31/17; A61K 31/535; C07C 127/19; C07D 295/20
[52] U.S. Cl. .................. 514/235; 514/234; 514/534; 514/538; 514/546; 514/595; 544/169; 560/34; 560/106; 560/251; 564/47
[58] Field of Search .................. 544/169; 560/34, 106, 560/251; 564/47; 514/235, 538, 546, 534, 595, 234

[56] References Cited

U.S. PATENT DOCUMENTS

| | | | |
|---|---|---|---|
| 3,928,412 | 12/1975 | Smith | 564/47 |
| 4,143,140 | 3/1979 | Main et al. | 564/47 |
| 4,425,362 | 1/1984 | Berthold | 564/48 |

FOREIGN PATENT DOCUMENTS

| | | |
|---|---|---|
| 0052072 | 5/1982 | European Pat. Off. . |
| 2458908 | 11/1975 | Fed. Rep. of Germany . |
| 2368951 | 11/1975 | France . |
| 1298017 | 11/1972 | United Kingdom . |
| 1455116 | 11/1976 | United Kingdom . |
| 2002748 | 2/1979 | United Kingdom . |

OTHER PUBLICATIONS

European Patent Application, 0041492, 12-9-81.

Primary Examiner—Robert W. Ramsuer
Attorney, Agent, or Firm—Brumbaugh, Graves, Donohue & Raymond

[57] ABSTRACT

Compounds of the formula

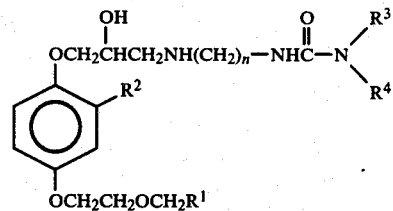

having beta receptor blocking properties, are disclosed.

18 Claims, No Drawings

PARA-SUBSTITUTED 3-PHENOXY-1-CARBONYLAMINO-ALKYLAMINO-PROPANOL COMPOUNDS, BETA RECEPTOR BLOCKING COMPOSITIONS AND USE

This application is a continuation of application Ser. No. 621,147, filed June 18, 1984, now abandoned, which is a continuation of application Ser. No. 482,266, filed Apr. 5, 1983, now abandoned, which is a continuation-in-part of application Ser. No. 450,006, filed Dec. 15, 1982, now abandoned.

TECHNICAL FIELD

The present invention relates to new compounds having β-receptor blocking activity and being beneficial for the treatment of cardiac disorders such as essential hypertension and angina pectoris, process for their preparation and pharmaceutical preparations containing the compounds mentioned. Generally the new compounds can be used in the treatment of all indications where beta-adrenoceptor blockers are used.

The object of the present invention is to obtain new compounds with beta-adrenoceptor blocking activity, characterized by a markedly selective affinity for $\beta_1$-adrenoceptors and a certain degree of intrinsic activity on cardiac beta-adrenoceptors. A cardioselective partial agonistic activity in combination with a cardioprotective beta-blocking effect is believed to be therapeutically advantageous in situations of anticipated heart failure. A cardiostimulatory effect level equal to 10–40 percent of what may be achieved at maximal isoprenaline stimulation is considered suitable for the indications in view.

A duration of action of at least 2–3 hours and a good availability at oral administration are further desired.

BACKGROUND OF THE INVENTION

Numerous compounds of the general structure

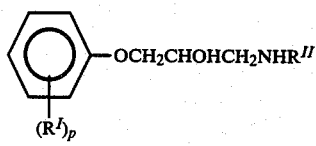

wherein the groups $R^I$ and $R^{II}$ and the integer p can be broadly varied, are known to possess beta-adrenoceptor blocking activity whereby they are used in treating angina pectoris, heart arrhythmias, hypertension, and glaucoma i.a.

DISCLOSURE OF THE INVENTION

It has been found that the compounds of the general formula

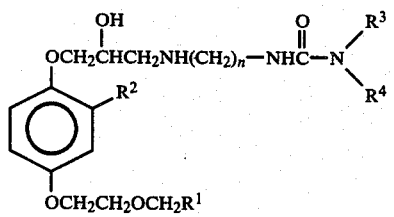

in which formula $R^1$ is H, a straight or branched alkyl group containing 1–5 carbon atoms, a cycloalkyl group containing 3–6 carbon atoms, or a cycloalkylalkyl group containing 4–16 carbon atoms;

$R^2$ is H, Cl, Br, or F;

n is 2, 3 or 4;

$R^3$ and $R^4$ are the same or different and each an alkyl group containing 1–4 carbon atoms, a hydroxyalkyl group containing 1–4 carbon atoms, an alkoxyalkyl group containing 2–4 carbon atoms in total, or $R^3$ and $R^4$ are both H or $R^3$ and $R^4$ together with the adjacent nitrogen atom form a morpholine group, and pharmaceutically acceptable acid addition salts thereof, are potent $\beta_1$-selective adrenoceptor blockers having a desired degree of intrinsic activity.

Alkyl $R^1$ has up to 5 carbon atoms, and can be straight or branched. Thus, alkyl $R^1$ can be e.g. methyl, ethyl, n-propyl, isopropyl, n-butyl, isobutyl, or n-pentyl.

Cycloalkyl $R^1$ has 3 to 6 carbon atoms and can thus be e.g. cyclopropyl, cyclobutyl, cyclopentyl, or cyclohexyl.

Cycloalkylalkyl $R^1$ has 4–6 carbon atoms and includes cyclopropylmethyl, 2-cyclopropylethyl and 2-cyclobutylethyl.

Alkyl $R^3$ and $R^4$ is each an alkyl group having up to 4 carbon atoms, which alkyl group can be straight or branched. Thus, alkyl $R^3$ and $R^4$ can each be e.g. methyl, ethyl, or n-propyl.

Hydroxyalkyl $R^3$ and $R^4$ can each be e.g. one of the alkyl $R^3$ and $R^4$ mentioned carrying a hydroxy group.

Alkoxyalkyl $R^3$ and $R^4$ can each be an alkoxyalkyl group having up to 3 carbon atoms in each alkyl part, which alkyl parts can be straight or branched. Alkoxyalkyl $R^3$ and $R^4$ can thus each be e.g. methoxyethyl, methoxypropyl or ethoxyethyl.

$R^3$ and $R^4$ in formula I are preferably other than hydroxymethyl and alkoxymethyl as those groups are easily split off and substituted by hydrogen. However, as such splitting, if occurring, forms other compounds of the invention said non-preferred compounds can be usable.

According to a preferred embodiment the invention relates to compounds of formula I wherein $R^1$ is H, $C_2H_5$, isopropyl or cyclopropyl. $R^2$ is preferably H and n is preferably 2.

Preferred compounds of the invention are those compounds of formula I in which $R^1$ is selected from hydrogen, ethyl, isopropyl and cyclopropyl, $R^2$ is H, n is 2 and $NR^3R^4$ is selected from N,N-dimethylamino and morpholino, and further those compounds of formula I in which $R^1$ is selected from hydrogen, ethyl, isopropyl or cyclopropyl, $R^2$ is H, n is 2 and $-NR^3R^4$ is selected from N-methoxyethyl-N-methylamino, N,N-dimethoxyethylamino, N-methyl-N-ethylamino and N,N-diethylamino.

Preferred compounds of the invention are in particular:

N—(2-((2-hydroxy-3-(4-(2-methoxyethoxy)phenoxy)propyl)-amino)ethyl)-4-morpholinecarboxamide -continued

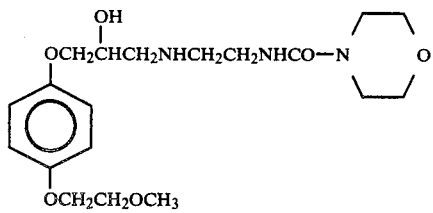

N—(2-((2-hydroxy-3-(4-(2-cyclopropylmethoxyethoxy)-phenoxy)propyl)amino)ethyl)-4-morpholinecarboxamide

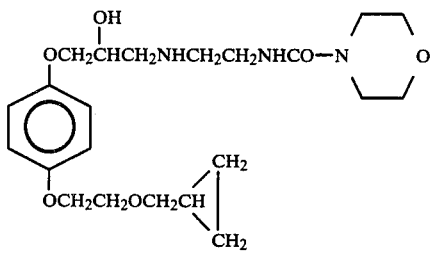

N—(2-((2-hydroxy-3-(4-(2-(2-methylpropoxy)ethoxy)-phenoxy)propyl)amino)ethyl)-4-morpholinecarboxamide

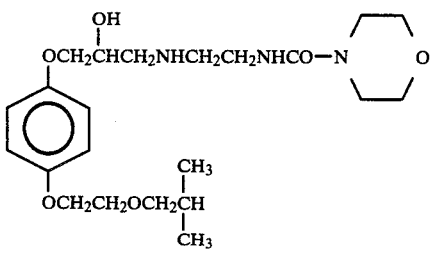

N—(2-((2-hydroxy-3-(4-(2-propoxyethoxy)phenoxy)propyl)-amino)ethyl)-4-morpholinecarboxamide

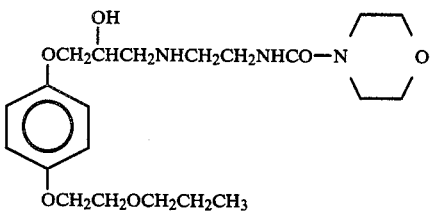

N,N—dimethyl-N'—(2-((2-hydroxy-3-(4-(2-(2-methyl-propoxy)ethoxy)phenoxy)propyl)amino)ethyl)-urea

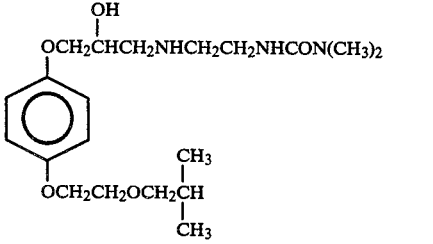

Further specific compounds of the invention are:
N-(2-((2-hydroxy-3-(4-(2-ethoxyethoxy)phenoxy)-propyl)amino)ethyl)-4-morpholinecarboxamide
N-(2-((2-hydroxy-3-(4-(2-cyclobutylmethoxyethoxy)-phenoxy)propyl)amino)ethyl)-4-morpholinecarboxamide
N-(2-((2-hydroxy-3-(4-(2-(2,2-dimethylpropoxy)ethoxy)phenoxy)propyl)amino)ethyl)-4-morpholinecarboxamide
N-(2-((2-hydroxy-3-(2-bromo-4-(2-ethoxyethoxy)-phenoxy)propyl)amino)ethyl)-4-morpholinecarboxamide
2-((2-hydroxy-3-(4-(2propoxyethoxy)phenoxy)propyl)amino)ethyl-urea
N,N-dimethyl-N'-(2-((2-hydroxy-3-(4-(2-cyclopropyl-methoxyethoxy)phenoxy)propyl)amino)ethyl)urea
N-(2-((2-hydroxy-3-(4-(2-(2-methylpropoxy)ethoxy)-phenoxy)propyl)amino)ethyl)-N'-2-methoxyethyl-N'-methyl-urea
N,N-diethyl-N'-(2-((2-hydroxy-3-(4-(2-methoxyethoxy)phenoxy)propyl)amino)ethyl)-urea
N,N-di-(2-methoxyethyl)-N'-(2-((2-hydroxy-3-(4-(2-methoxyethoxy)phenoxy)propyl)amino)ethyl)-urea The invention takes into consideration that a compound which structurally deviates from the formula I, after administration to a living organism may be transformed to a compound of the formula I and in this structural form exert its effect.

Thus, a compound derived from formula I or a pharmaceutically acceptable salt thereof, in which formula $R^1$, $R^2$, n, $R^3$ and $R^4$ are as defined in claim 1, in which compound the hydroxy group in the phenoxypropanolamine chain is acylated with a splitable innocuous acyl residue and/or the nitrogen atom in the phenoxypropanolamine chain and/or the monoalkylated amidic nitrogen is acylated or alkylated with a splitable innocuous acyl or acyloxyalkyl residue, may after administration to a living organism be deacylated and/or dealkylated to a compound of the formula I.

Such prodrugs or bioprecursors to compounds of the formula I are in particular compounds of the formula

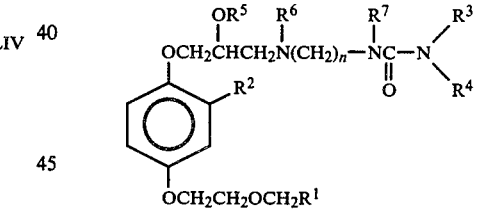

and pharmaceutically acceptable salts thereof, wherein $R^5$, $R^6$ and $R^7$ may be the same or different and $R^5$ is H or $R^8CO$, wherein $R^8$ is an aliphatic group such as a straight or branched alkyl group having 1 to 4 carbon atoms such as methyl, ethyl, n-propyl, iso-propyl, sec. butyl or tert. butyl, or an aromatic group such as phenyl or substituted phenyl e.g. 2,6-dimethylphenyl; $R^6$ is a group $R^5$ as defined above or $R^6$ is $R^9CO$ or

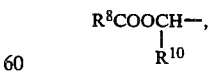

wherein $R^9$ is —$CH_2CH_2COOR^8$ or —$CH_2CH_2CH_2OCOR^8$ and $R^8$ is as defined above and $R^{10}$ is hydrogen, methyl or ethyl; and $R^7$ is a group $R^6$ as defined above, provided that at least one of $R^5$, $R^6$ and $R^7$ is other than hydrogen.

Specific compounds regarded as prodrugs to compounds of formula I are

N—[2-[[2-benzoyloxy-3-[4-(2-methoxyethoxy)phenoxy]propyl]-amino]ethyl]-4-morpholinecarboxamide

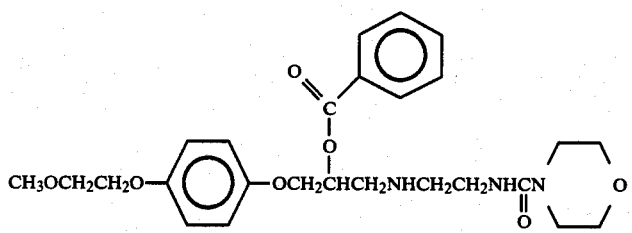

LX

N—[2-[[2-hydroxy-3-[4-(2-methoxyethoxy)phenoxy]propyl]-(2,2-dimethylpropanoyloxymethyl)amino]ethyl]-4-morpholine-carboxamide

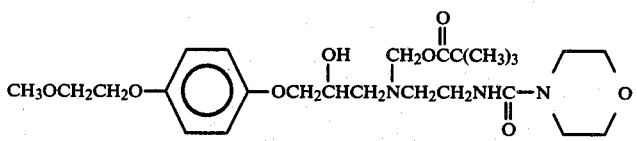

LXI

N—[2-[[2-hydroxy-3-[4-(2-methoxyethoxy)phenoxy]propyl]amino]-ethyl]-N—[2,2-dimethylpropanoyloxymethyl]-4-morpholine-carboxamide

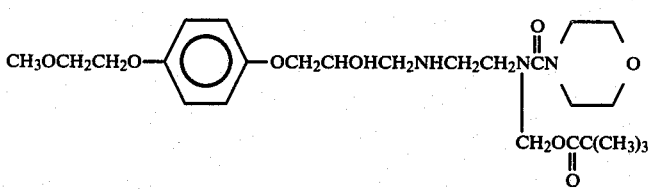

LXII

N—[2-[[2-hydroxy-3-[4-(2-methoxyethoxy)phenoxy]propyl]-[4-(ethanoyloxy)butanoyl]amino]ethyl]-4-morpholinecarboxamide

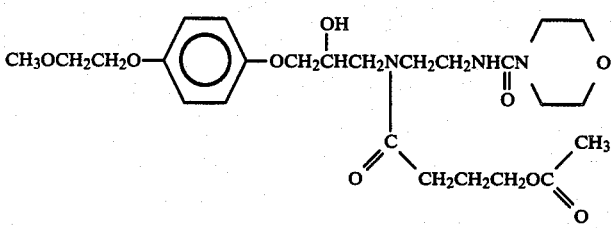

LXIII

In addition to the compounds of formula I above the following compounds have been found to be useful for similar purposes as the compounds of formula I:

N—(2-((2-hydroxy-3-(4-(2-(2-methylpropoxy)-ethoxy)phenoxy)propyl)amino)-ethyl)-N'—methyl-urea

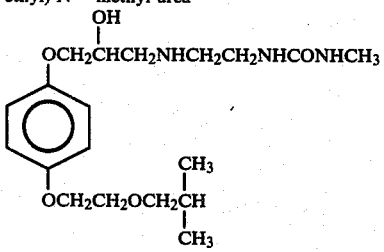

LV

N—(2-((2-hydroxy-3-(4-(2-propoxyethoxy)-phenoxy)propyl)amino)ethyl)-N'—methyl-urea -continued

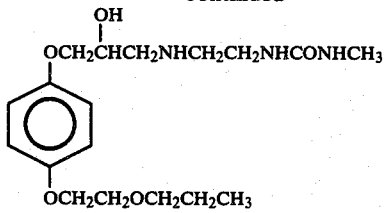

LVII

N—(2-((2-hydroxy-3-(4-(2-methoxyethoxy)-phenoxy)propyl)amino)-ethyl)-N'—methyl-urea

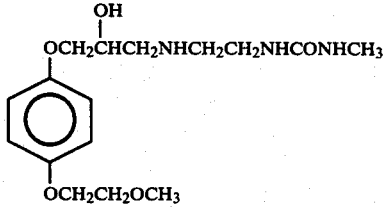

LIX

N—(2-((2-hydroxy-3-(4-(2-(2-methylpropoxy)-

-continued
ethoxy)phenoxy)propyl)amino)-
ethyl)-N'—2-methoxyethyl-urea

LVIII

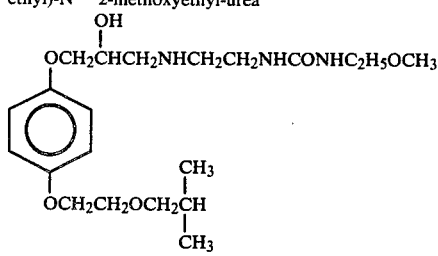

The compounds of the invention can be used at the treatment as outlined above. One may also use them as intermediates at the preparation of other valuable pharmaceutical compounds.

Salt forming acids may be used in preparing therapeutically acceptable salts of the compounds. These are: hydrohalogen acids, sulfuric acid, phosphoric acid, nitric acid, perchloric acid, aliphatic, alicyclic, aromatic or heterocyclic carboxy or sulfonic acids, such as formic, acetic, propionic, succinic, glycolic, lactic, malic, tartaric, citric, ascorbic, maleic, hydroxymaleic, or pyrovic acid, phenylacetic, benzoic, p-aminobenzoic, anthranilic, p-hydroxybenzoic, salicyclic or p-aminosalicyclic acid, pamoic acid, methanesulfonic, ethanesulfonic, hydroxyethanesulfonic, ethylenesulfonic, halogenbenzenesulfonic, toluenesulfonic, napthylsulfonic, or sulfanilic acid, methionine, tryptophane, lysine or arginine.

Below, for convenience, the part of formula I

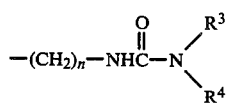

is referred to as $R^N$ and the part of formula I

—CH$_2$CH$_2$OCH$_2$R$^1$ is referred to as $R^0$. In the groups $R^N$ and $R^0$ the groups $R^1$, $R^3$, $R^4$ and n are as defined in connection with the specified formulas. Unless specified otherwise $R^2$ below is as defined in connection with the specified formulas.

The new compounds of the formula I are obtained according to methods such as the following.

(a) Reacting a compound of the formula

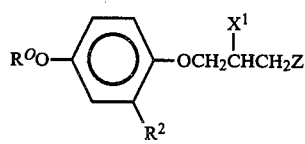
II

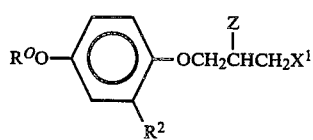
IIa wherein $X^1$ is hydroxy group, Z is a hydroxy group or a reactive, esterified hydroxy group, or $X^1$ and Z together form an epoxy group, with a compound of the formula

H$_2$NR$^N$
III

When Z is a reactive, esterified hydroxy group, it is particularly a hydroxy group esterified with a strong, inorganic or organic acid, preferably a hydrohalogen acid, such as hydrochloric acid, hydrobromic acid, or hydroiodic acid, further sulfuric acid or a strong organic sulfonic acid, e.g. methanesulfonic, trifluoromethanesulfonic, benzenesulfonic, 4-bromobenzenesulfonic or 4-toluenesulfonic acid. Z is preferably chloro, bromo, iodo, methanesulfonyl, trifluoromethanesulfonyl or 4-toluenesulfonyl.

At the use of a reactive ester as a starting material the reaction is preferably carried out in the presence of a basic condensating agent and/or with an excess of an amine. Suitable basic condensating agents are e.g. alkali metal hydroxides such as sodium or potassium hydroxide, alkali metal carbonates such as potassium carbonate, and alkali metal alcoholates such as sodium methylate, potassium ethylate or potassium tert. butylate.

Ring closure to an epoxide may occur as an intermediary reaction is employing a compound of formula II or IIa wherein Z is a reactive esterified hydroxy group. When both Z and $X^1$ are —OH the reaction is carried out in the presence of a metal catalyst, such as Raney nickel. The reaction is preferably carried out in a solvent, which is for example an alkanol having 1 to 4 carbon atoms, by refluxing the reactants in said solvent for a time sufficiently long to give the desired compound, generally 3 to 24 hours.

(b) Reacting a compound of the formula

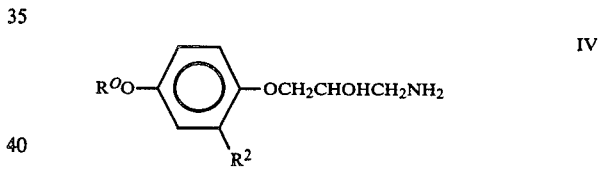
IV wherein $R^1$ and $R^2$ are as defined above, with a compound of the formula

ZR$^N$
V wherein Z is as defined above.

This reaction is carried out preferably in the presence of a basic condensating agent and/or excess of an amine. Suitable basic condensating agents are e.g. alkaline alcoholates, preferably sodium or potassium alcoholate, or alkaline carbonates such as sodium or potassium carbonate.

The reaction is suitably carried out in an autoclave being heated to 100° to 130° C. for 5 to 15 hours with or without the presence of an alkanol having 1 to 3 carbon atoms as solvent.

(c) Reacting a compound of the formula

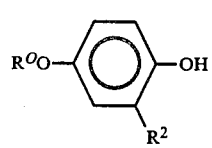
VI with a compound of formula

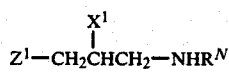

VII wherein $X^1$ is as defined above, and $Z^1$ is Z as defined above however $Z^1$ is other than hydroxy.

When a reactive ester is used as starting material, the compound of formula VI may suitably be used in the form of its metal phenolate such as an alkali metal phenolate, preferably sodium phenolate. The reaction can also be carried out in the presence of an acid binding agent, preferaby a condensating agent, which can form a salt, such as an alkali metal alcoholate of the compound of formula VI.

The reaction is preferably carried out in an autoclave being heated to 80° to 100° C. for 1 to 15 hours in an alkanol having 1 to 3 carbon atoms as solvent.

(d) Reacting a compound of the formula

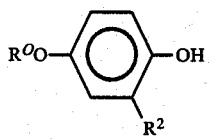

VI with a compound of the formula

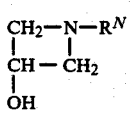

VIII

The reaction is suitably carried out under alkaline conditions in a suitable solvent such as benzyl alcohol by boiling the reaction mixture for some hours. Thereby the phenol VI is primarily converted to its metal phenolate such as an alkali metal phenolate before it is added to the azetidinol of formula VIII.

(e) Reacting a compound of the formula

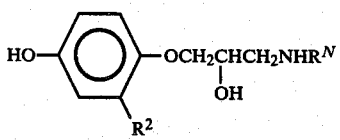

IX with a compound of the formula

X wherein $Z^1$ is as defined above.

(f) Reacting a compound of the formula

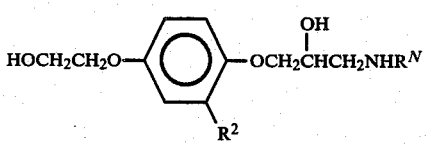

XI with a compound of the formula

XII wherein $R^1$ and $Z^1$ are as defined above.

(g) Reacting a compound of the formula

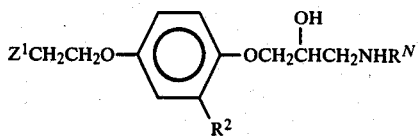

XIII wherein $Z^1$ is as defined above, with a compound of the formula $R^1CH_2OH$  XIV wherein $R^1$ is as defined above.

In the reactions e, f and g, the reacting hydroxy group is typically activated by a base. The reactions e, f and g are preferably carried out in a polar aprotic medium.

(h) Reacting a compound of the formula

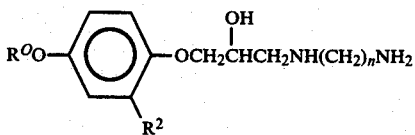

XV wherein n is as defined above, with a compound of the formula

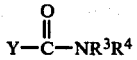

XVI wherein $R^3$ and $R^4$ are as defined above and Y is a leaving group such as halogen, alkoxy, an aryloxy group or an acyloxy group.

(i) Reacting a compound of the formula

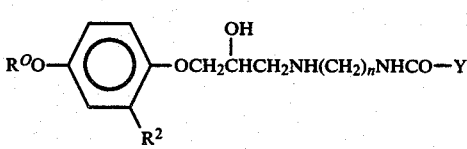

XVII wherein n and Y are as defined above, with a compound of the formula $MNR^3R^4$  XVIII wherein $R^3$ and $R^4$ are as defined above and M is H or a metal.

(j) Reacting a compound of the formula

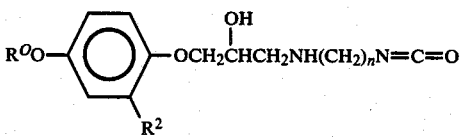

XIX wherein n is as defined above, with a compound of the formula $MNR^3R^4$  XVIII wherein M, $R^3$ and $R^4$ are as defined above.

(k) Reacting a compound of the formula

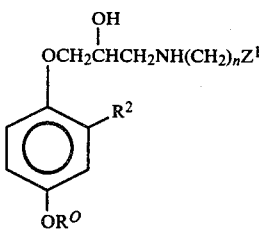

wherein n and $Z^1$ are as defined above, with a compound of the formula $$H_2NCONR^3R^4 \quad XXI$$

wherein $R^3$ and $R^4$ are as defined above. The reaction is preferably carried out under alkaline conditions.

(l) Reacting a compound of the formula XV above, wherein $R^1$, $R^2$, and n are as defined above, with a compound of the formula $$H_2NCONR^3R^4 \quad XXI$$

wherein $R^3$ and $R^4$ are as defined above. The reaction is preferably carried out with the compound XV in its hydrochloride form and with water as solvent. The reaction mixture is refluxed for about 1–5 hours.

(m) For the preparation of a compound of the formula I wherein $-NR^3R^4$ is morpholino, subjecting a compound of the formula

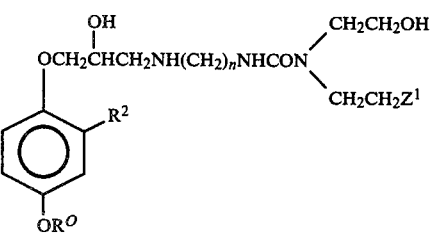

wherein n and $Z^1$ are as defined above, to cyclization whereby the group

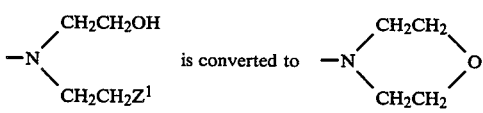

The reaction is preferably carried out under alkaline conditions.

(n) Reacting a compound of the formula

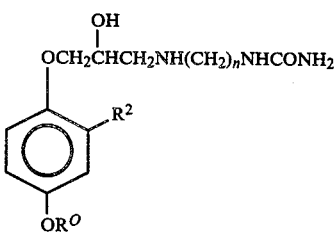

wherein n is as defined above, with a compound of the formula $$MNR^3R^4 \quad XVIII$$

wherein M, $R^3$ and $R^4$ are as defined above, or, for preparation of a compound of formula I wherein $-NR^3R^4$ is morpholine, with a compound of the formula $$Z^1(CH_2)_2O(CH_2)_2Z^1 \quad XXIII$$

wherein $Z^1$ is as defined above.

The reaction is preferably carried out under basic conditions.

(o) For the preparation of a compound of the formula I wherein $-NR^3R^4$ is morpholino, reacting a compound of the formula

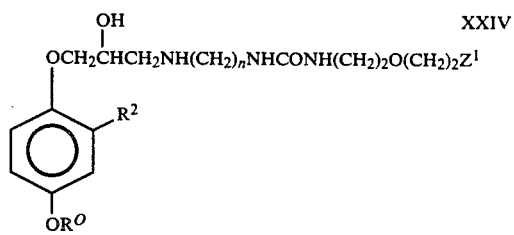

wherein n and $Z^1$ are as defined above, under alkaline conditions. The compound of formula XXIV occurs as an intermediate in the reaction between compounds XXII and XXIII under (n) above.

(p) Subjecting a compound of the formula

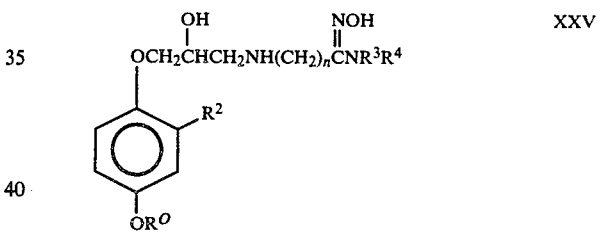

wherein n, $R^3$ and $R^4$ are as defined above, to the Beckmann rearrangement to give a compound of the formula I.

(q) Splitting off a residue from a compound of formula I above, in which one or more of the nitrogen atoms and/or a hydroxy group have attached thereto a splitable residue.

Such splitable residues are especially those which are splitable by solvolysis, reduction, pyrolysis or fermentation.

Residues splitable by means of hydrolysis are e.g. acyl residues, which, when present, also can be functionally varied carboxy groups, e.g. oxycarbonyl residues, such as alkoxycarbonyl residues, e.g. tert. butoxycarbonyl residue, or ethoxycarbonyl residue, aralkoxycarbonyl residues such as phenylloweralkoxycarbonyl residues, e.g. a carbobenzyloxy residue, halogencarbonyl residue, e.g. a chlorocarbon residue, and carbamoyl groups. Further, arylsulfonyl residues such as toluenesulfonyl or bromobenzenesulfonyl residues and possibly halogenated, e.g. possibly fluorinated, lower alkanoyl residues such as formyl, acetyl, or trifluoroacetyl residues or a benzyl residue or cyano groups or silyl residues, such as trimethylsilyl residue, are residues splitable by means of hydrolysis.

Of the above mentioned residues present at the hydroxy groups, which residues are splitable by hydrolysis, preferably the oxycarbonyl residues and the loweralkanoyl residues or the benzoyl residues are used.

Besides the above mentioned also double-bound residues, which are splitable at the amino group by hydrolysis are used, e.g. alkylidene or benzylidene residue or a phosphorylidene group as a triphenylphosphorylidene group, whereby the nitrogen atom then obtains a positive charge.

Residues splitable at the amino group by hydrolysis are furthermore divalent residues such as substituted methylene. As substituents on the methylene residues any organic residue may be used, whereby it does not matter at the hydrolysis which compound is the substituent to the methylene residue. As methylene substituents e.g. aliphatic or aromatic residues as alkyl as mentioned above, aryl e.g. phenyl or pyridyl may be used. The hydrolysis may be carried out in any common way, suitably in a basic or preferably in an acid medium.

Compounds having residues being splitable by hydrolysis are also the compounds according to the formula

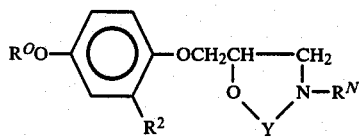   XXVI wherein Y is a carbonyl, thiocarbonyl, or a

residue wherein A and B are each hydrogen, alkyl, alkylaryl or aryl.

The hydrolysis is carried out in a customary way, e.g. in the presence of a hydrolysing agent, e.g. in the presence of an acidic agent as e.g. diluted mineral acids, such as sulfuric acid or hydrohalogen acid, or in the presence of basic agents as e.g. alkali metal hydroxides, such as sodium hydroxide. Oxycarbonyl residues, aryl sulfonyl residues and cyano groups may in a suitable way by split off by means of acidic agents such as by means of a hydrohalogen acid, suitably hydrobromic acid. Preferably the splitting may take place using diluted hydrobromic acid, possibly in a mixture with acetic acid. Cyano groups are preferably split off by means of hydrobromic acid at an elevated temperature, as in boiling hydrobromic acid, according to the "bromo-cyano method" (v. Braun). Further, e.g. a tert.- butoxycarbonyl residue may be split off under anhydrous conditions by means of a treatment with a suitable acid, as trifluoroacetic acid. Acidic agents are preferably used at a hydrolysis of compounds of formula XXVI.

Residues splitable by ammonolysis are especially the halogencarbonyl residues, such as the chlorocarbonyl residue. The ammonolysis may be carried out in a common way, e.g. by means of an amine containing at least one hydrogen atom bound to the nitrogen atom, as a mono- or diloweralkylamine, e.g. methylamine or dimethylamine, or especially ammonia, preferably at an elevated temperature. Instead of ammonia one may use an agent which gives ammonia such as hexamethylenetetraamine.

Residues splitable by means of a reduction are e.g. an α-arylalkyl residue, such as a benzyl residue or an α-aralkoxycarbonyl residue such as a benzyloxycarbonyl residue, which in a common way may be split off by means of a hydrogenolysis, especially by catalytically activated hydrogen, e.g. by hydrogen in the presence of hydrogenating catalysts e.g. Raney nickel or by electrochemical reduction. Further residues splitable by means of hydrogenolysis are 2-halogenalkoxycarbonyl residues such as 2,2,2-trichloroethoxycarbonyl residues or 2-iodoethoxy- or 2,2,2-tri-bromoethoxycarbonyl residues, which may be split off in a common way, suitably by means of a metallic reduction (so called nascerating hydrogen). Nascerating hydrogen may be obtained by the influence of metal or metal alloys, such as amalgam on compounds which give hydrogen as carboxy acids, alcohols or water, whereby especially zink or zinkalloys together with acetic acid may be used. Hydrogenolysis of 2-halogenalkoxycarbonyl residues may further take place using chromium or chromium (II) compounds as chromium (II) chloride or chromium (II) acetate.

A residue splitable by reduction may also be an arylsulfonyl group such as a toluenesulfonyl group, which in a common way may be split off electrochemically or by reduction using nascerating hydrogen, e.g. by means of an alkali metal, as lithium or sodium in liquid ammonia, and suitably may be split off from a nitrogen atom. At the carrying out of the reduction one has to take care that other reducible groups are not influenced.

Residues splitable by means of pyrolysis, especially residues splitable from the nitrogen atom, are in occurring cases substituted suitably unsubstituted carbamoyl groups. Suitable substituents are e.g. loweralkyl or aryl-loweralkyl, such as methyl or benzyl, or aryl, such as phenyl. The pyrolysis is carried out in a common way, whereby one may have to take care of other termically susceptible groups.

Residues splitable by means of fermentation, especially residues splitable from the nitrogen atom are in occurring cases substituted, however, suitably unsubstituted carbamoyl groups. Suitable substituents are e.g. loweralkyl or aryl-loweralkyl, such as methyl or benzyl, or aryl such as phenyl. The fermentation is carried out in a common way, e.g. by means of the enzyme urease or soy bean extract at about 20° C. or slightly elevated temperature.

(r) Converting a compound of the formula

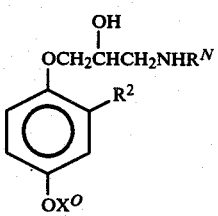   XXVII wherein $X^0$ is a group containing one or more carbon-carbon unsaturation and being convertible to the group $R^0$ by saturating each such unsaturation therein.

(s) Reducing a Schiff's base of one of the formulas

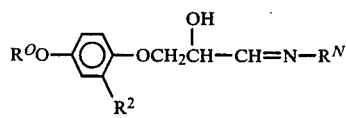

XXVIII

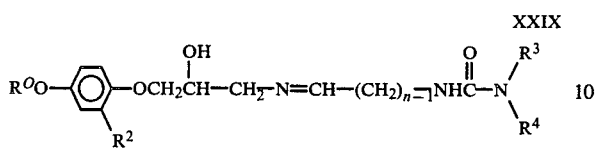

XXIX or a cyclic tautomer corresponding to formula XXIX, said tautomer of the formula

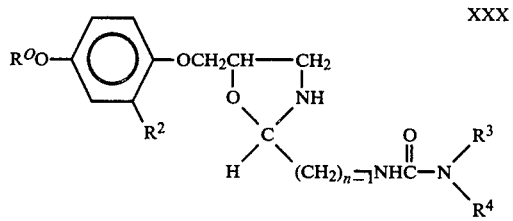

XXX wherein $R^3$, $R^4$ and n having the same meanings as given above, and whereby the compounds of the formula XXIX and XXX may exist together.

This reduction is carried out in a common way, e.g. using a di-lightmetalhydride, using a hydride such as a borane with formic acid, or by means of a catalytic hydrogenation, e.g. with hydrogen in the presence of Raney nickel. At the reduction one has to take care that other groups are not affected.

(t) Reducing the oxo group to a hydroxy group in a compound of formula

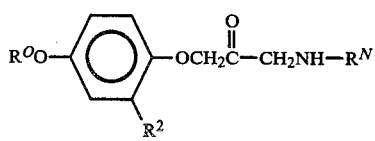

XXXI

This reduction is carried out in a common way, especially using a di-lightmetalhydride, as mentioned above, or according to the "Meerwein-Pondorf-Verley method" or a modification thereof, suitably using an alkanol as a reaction component and as solvent, e.g. isopropanol, and using a metalalkanolate, such as metalisopropanolate, e.g. aluminium isopropanolate.

(u) Reducing an amidic carbonyl group in a compound of one of the formulas

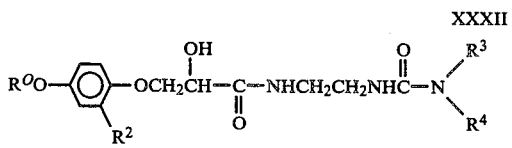

XXXII

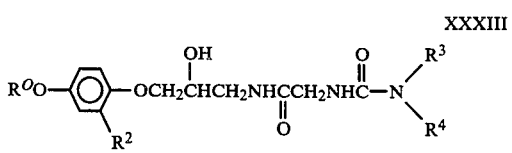

XXXIII

The reduction can be carried out according to the above described manner using complex metal hydrides, e.g. lithium aluminium hydride or di-isobutylaluminium hydride. Suitably the reaction takes place in an inert solvent as an ether, e.g. diethyl ether or tetrahydrofuran. Complex borohydrides can also be used especially when a selective reaction is wanted.

(v) Transforming in a compound of the formula

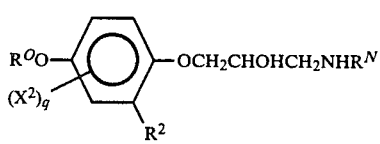

XXXVI wherein q is an integer 1 to 4 and $X^2$ can be in one or more of the 2, 3, 5 and 6 positions, and $X^2$ is a splitable residue, or $X^2$ is hydrogen, or $X^2$ in the position of $R^2$ is a residue transformable into $R^2$, one or more residue $X^2$ is split off and/or $R^2$ is introduced or $X^2$ is transformed into $R^2$.

Thus, a compound of the present invention can be obtained by catalytic hydrogenation of a compound of the invention containing one or more substituents in the aromatic ring that can be split off by means of catalytic hydrogenation. Such substituents are F, Br, Cl and I. The splitting off can also take place in connection with prior mentioned methods.

Depending on the process conditions and the starting material the end product is obtained either in free form or in the form of its acid addition salt, which is included in the scope of the invention. Thus, for example, basic, neutral or mixed salts may be obtained as well as hemiamino, sesqui- or polyhydrates. The acid addition salts of the new compounds may in a manner known per se be transformed into free compounds using e.g. basic agents as alkali or ion exchanger. On the other hand, the free bases obtained may form salts with organic or inorganic acids. In the preparation of acid addition salts preferably such acids are used which form suitable pharmaceutically acceptable salts. Examples of such acids are given above.

These or other salts of the new compounds as e.g. picrates may serve as purifying agents for the free bases obtained as the free bases are transformed into salts, these are separated and the bases are then set free from the salts again. According to the close relationship between the new compounds in free form and in the form of their salts it will be understood from the above and the below that, if possible and unless specified otherwise, reference to the free compound should be taken as a reference to the corresponding salts as well.

The invention also relates to any embodiment of the process in which one starts from any compound obtained as an intermediate in any process step and one carries out the lacking process step, or one breaks off the process at any step, or at which one forms a starting material under the reaction conditions, or at which a reaction component possibly in the form of its salts is present.

Thus, one may react an aldehyde of the formula

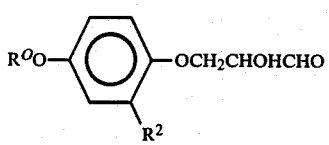             XXXIV with an amine of the formula $H_2NR^4$                                           III in the presence of a suitable reducing agent, such as one of the above mentioned. Thereby, a compound of formula XXVIII is obtained as an intermediate, which is reduced according to the invention.

Further, one may in a manner known per se react an amine of the formula IV above with a compound of the formula

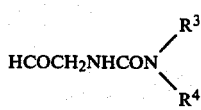             XXXV in the presence of a suitable reducing agent, such as one of the above mentioned, to produce compounds of formula XXIX or XXX as an intermediate, which are reduced according to the invention.

For the preparation of a compound derived from formula I, in which the hydroxy group in the phenoxypropanolamine chain is acylated with a splitable innocuous acyl residue and/or the nitrogen atom in the phenoxypropanolamine chain and/or the monoalkylated amidic nitrogen is acylated or alkylated with a splitable innocuous acyl or acyloxyalkyl residue, the compound of formula I or one or more precursors of said compound as defined above is acylated or alkylated whereupon when required the remaining process steps defined above are carried out.

For the preparation of a compound of one of the formulas LV, LVII, LVIII and LIX one or more precursors defined above having the appropriate group $R^0$ and having the group $-NR^3R^4$, which may be a part of $R^N$, replaced with one of the groups $-NHCH_3$ or $-NHC_2H_5OCH_3$ are made subject to a process described above.

As the new compounds of the invention possess at least one asymmetric carbon atom, the invention includes all the possible isomers of the compounds. The new compounds may thus, depending on the choice of starting materials and process, be present as optical antipodes or racemate, or, if they contain at least two asymmetric carbon atoms, be present as an isomer mixture (racemate mixture).

The isomer mixtures (racemate mixtures) obtained may depending on physical-chemical differences of the component, be separated into the both stereoisomeric (diastereomeric) pure racemates e.g. by means of chromatography and/or fractionated crystallization.

The racemates obtained can be separated according to known methods, e.g. by mans of recrystallization from an optically active solvent, by means of microorganisms, or by a reaction with optically active acids forming salts of the compound and separating the salts thus obtained, e.g. by means of their different solubility in the diastereomers, from which the antipodes by the influence of a suitable agent may be set free.

Suitably useable optically active acids are e.g. the L- and D-forms of tartaric acid, di-o-tolyl-tartaric acid, malic acid, mandelic acid, camphersulfonic acid or quinic acid. Preferably the more active part of the two antipodes is isolated. Further one of the two enantiomers can be obtained by asymmetrical reduction of the corresponding keto-compound.

Suitably such starting materials are used for carrying out the reactions of the invention, which material leads to groups of end products primarily especially desired and especially to the specifically described and preferred end products.

The starting materials are known or may, if they should be new, be obtained according to processes known per se.

In clinical use the compounds of the invention are administered normally orally, rectally or by injection in the form of a pharmaceutical preparation, which contains an active component either as free base or as pharmaceutically acceptable, non-toxic acid addition salts, e.g. the hydrochloride, lactate, acetate, sulphamate or the like in combination with a pharmaceutical carrier.

The carrier may be a solid, semisolid or liquid diluent or a capsule. These pharmaceutical preparations are a further object of the invention. Usually the amount of active compound is between 0.1 to 99% by weight of the preparation, suitably between 0.5 to 20% by weight in preparations for injection and between 2 to 50% by weight in preparations for oral administration.

In the preparation of pharmaceutical preparations containing a compound of the present invention in the form of dosage units for oral administration the compound elected may be mixed with a solid, pulverulent carrier, as e.g. with lactose, saccharose, sorbitol, mannitol, starch such as potato starch, corn starch, amylopectin, cellulose derivatives or gelatine, as well as with an antifriction agent as mgnesium stearate, calcium stearate, polyethyleneglycol waxes, or the like, and be pressed into tablets. If coated tablets are wanted, the above prepared core may be coated with a concentrated solution of sugar, which solution may contain e.g. gum arabicum, gelatine, talc, titandioxide or the like. Furthermore, the tablets may be coated with a lacquer dissolved in an easily volatile organic solvent or mixture of solvents. To this coating a dye may be added in order to easily distinguish between tablets with different active compounds or with different amounts of the active compound present.

In the preparation of soft gelatine capsules (pearl-shaped, closed capsules), which consist of gelatine and e.g. glycerine or in the preparation of similar closed capsules the active compound is mixed with a vegetable oil. Hard gelatine capsules may contain granules of the active compound in combination with a solid, pulverulent carrier as lactose, saccharose, sorbitol, mannitol, starch (as e.g. potato starch, corn starch or amylopectin), cellulose derivatives or gelatine.

Dosage units for rectal administration may be prepared in the form of suppositories, which contain the active substance in a mixture with a neutral fat base, or they may be prepared in the form of gelatine-rectal capsules which contain the active substance in a mixture with a vegetable oil or paraffin oil.

Liquid preparations for oral administration may be present in the form of sirups or suspensions, e.g. solutions containing from about 0.2% by weight to about 20% by weight of the active substance described, whereby the residue consists of sugar and a mixture of ethanol, water, glycerol, and propylene glycol. If desired, such liquid preparations may contain colouring agents, flavouring agents, saccharine and carboxymethyl cellulose as a thickening agent.

Solutions for parenteral administration by injection may be prepared as an aqueous solution of a water-soluble pharmaceutically acceptable salt of the active compound, preferably in a concentration from about 0.5% by weight to about 10% by weight. These solutions may also contain stabilizing agents and/or buffering agents and may suitably be available in different dosage unit ampoules.

The preparation of pharmaceutical tablets for peroral use is carried out in accordance with known methods.

The daily dose of the active substance varies and is depending on the type of administration, but as a general rule it is 20 to 500 mg/day at peroral administration and 10 to 200 mg/day at intravenous administration.

BEST MODE OF CARRYING OUT THE INVENTION

The following illustrates the principle and the adaption of the invention, however, without being limited thereto. Temperature is given in degrees Celsius.

EXAMPLE 1

Preparation of N-(2-((2-hydroxy-3-(4-(2-methoxyethoxy)-phenoxy)-propyl)amino)ethyl)-4-morpholinecarboxamide (Method a)

4 g of 3-(4-(2-methoxyethoxy)phenoxy)-1,2-epoxypropane, 5.8 g of the sulphate of N-2-aminoethyl-4-morpholinecarboxamide, and 5.8 g of $K_2CO_3$ were refluxed in 2-propanol for 2 days. The mixture was filtered and concentrated in vacuo. The residue was dissolved in methylene chloride and washed with $H_2O$. The organic phase was dried over $Na_2SO_4$, filtered and evaporated. The product was recrystallized from ethyl acetate. Yield 2.3 g. Melting point 69° C. (base). The structure was determined using NMR and equivalent weight.

EXAMPLE 2

Preparation of N-(2-((2-hydroxy-3-(4-(2-ethoxyethoxy)-phenoxy)-propyl)amino)ethyl)-4-morpholinecarboxamide (Method a)

12.0 g of the neutral sulphate of N-2-aminoethyl-4-morpholinecarboxamide, 2.16 g NaOH and 100 ml of absolute ethanol were refluxed 1 h. During continuing reflux 8.6 g of 3-(4-(2-ethoxyethoxy)phenoxy)-1,2-epoxypropane in 50 ml of abs. ethanol was added little by little. The resulting mixture was refluxed over night, filtered and evaporated. The residue was dissolved in 200 ml of ethyl acetate and extracted twice with water. The water phase was treated with NaCl and extracted twice with ethyl acetate. The ethyl acetate phase was dried, filtered and evaporated. The residue was crystallized from ether, and recrystallized from ethyl acetate. Yield 1.1 g. Melting point 75°–77° C. (base). The structure was determined using NMR analysis.

EXAMPLE 3

Preparation of N-(2-((2-hydroxy-3-(4-(2-cyclopropylmethoxyethoxy)-phenoxy)propyl)amino)ethyl)-4-morpholinecarboxamide (Method a)

26.2 g of the hydrochloride of N-2-aminoethyl-4-morpholinecarboxamide and 5.0 g of NaOH were refluxed in 175 ml of ethanol for 1 h. Thereafter 22 g of 3-(4-(2-cyclopropylmethoxyethoxy)phenoxy)-1,2-epoxypropane in 100 ml of ethanol was added and the resulting mixture refluxed for 16 h, filtered, and evaporated. The residue was dissolved in 300 ml of ethyl acetate and washed three times with water. The organic phase was then extracted with 250 ml of water at pH 5 (HCl). The aqueous phase was then made alkaline and extracted with methylene chloride. The methylene chloride phase was dried over $Na_2SO_4$, filtered, and evaporated. The residue was treated with ether and recrystallized from ethyl acetate. Yield 8.0 g. Melting point 80°–81° C. (base). The structure was determined using NMR-analysis.

EXAMPLE 4

Preparation of N-(2-((2-hydroxy-3-(4-(2-cyclobutylmethoxyethoxy)-phenoxy)propyl)amino)ethyl)-4-morpholinecarboxamide 12.0 g of the neutral sulphate of N-2-aminoethyl-4-morpholinecarboxamide and 2.16 g NaOH was refluxed in 100 ml of ethanol for 1 h. Thereafter 10 g of 3-(4-(2-cyclobutylmethoxyethoxy)phenoxy-1,2-epoxypropane in 50 ml of ethanol was added and the mixture refluxed for 20 h, filtered, and evaporated. The residue was dissolved in 175 ml of ethyl acetate and washed twice with water. Thereafter the title compound crystallized from the ethyl acetate phase. The crystals were filtered off and washed with ether. Yield 7.1 g. Melting point 91°–93° C. (base). The structure was determined using NMR-analysis.

EXAMPLE 5

N-(2-((2-hydroxy-3-(4-(2-(2-methylpropoxy)ethoxy)-phenoxy)propyl)amino)ethyl)-4-morpholinecarboxamide was prepared in accordance with example 4 using 10.1 g of the neutral sulphate of N-2-aminoethyl-4-morpholinecarboxamide and 9.3 g of 3-(4-(2-(2-methylpropoxy)ethoxy)phenoxy-1,2-epoxypropane as starting materials. Yield 3.9 g. Melting point 95°–96° C. (base). The structure was determined using NMR-analysis.

EXAMPLE 6

(Method b)

12 g of 1-amino-3-(4-(2-methoxyethoxy)phenoxy)-propanol-2, 20 g of N-(2-bromoethyl)-4-morpholinecarboxamide, and 7 g of $K_2CO_3$ were refluxed in acetonitril for 24 h, filtered, and evaporated. The residue was dissolved in methylene chloride and extracted with water at pH 4 ($H_2SO_4$). The water phase was extracted once more with methylene chloride, made alkaline and extracted twice with methylene chloride. The combined methylene chloride phase was dried over $Na_2SO_4$, filtered, and evaporated. The residue was crystallized from ethyl acetate yielding N-(2-((2-hydroxy-3-(4-(2-methoxyethoxy)phenoxy)propyl)amino)ethyl)-4-morpholinecarboxamide. Melting point 69° C. (base).

EXAMPLE 7

(Method c)

1.2 g of Na was dissolved in 100 ml of ethanol, whereupon 8.4 g of 4-(2-methoxyethoxy)phenol and 13.3 g of N-(2-((3-chloro-2-hydroxy)propyl)amino)ethyl-4-morpholinecarboxamide were added. The mixture was heated in an autoclave on a boiling waterbath for 10 hours. Thereupon it was filtered and the filtrate was evaporated to dryness. The residue was made acid to pH 3 using HCl and extracted with ether, whereupon the aqueous phase was made alkaline with ammonia and extracted with methylene chloride. The methylene chloride phase was dried over $MgSO_4$, filtered, and evaporated. N-(2-((2-hydroxy-3-(4-(2-methoxyethoxy)phenoxy)propyl)amino)ethyl)-4-morpholinecarboxamide was crystallized by treating the residue with ethyl acetate. Melting point 69° C. (base).

EXAMPLE 8

(Method d)

0.12 moles of 4-(2-methoxyethoxy)phenol was mixed with 0.080 moles of 1-(2-(4-morpholinecarboxamido)ethyl)-3-azetidinol, 0.500 moles of benzylalcohol and 0.002 moles of KOH. The mixture was refluxed while stirring for 6 hours at 140° C. and was then cooled and extracted with 1N HCl. The aqueous phase was made alkaline, and was finally extracted with methylene chloride. After drying, filtering and evaporating, N-(2-((2-hydroxy-3-(4-(2-methoxyethoxy)phenoxy)propyl)amino)ethyl)-4-morpholinecarboxamide was crystallized from ethyl acetate. Melting point 69° C. (base).

EXAMPLE 9

(Method e)

17 g of N-(2-((2-hydroxy-3-(4-hydroxyphenoxy)propyl)amino)ethyl)-4-morpholinecarboxamide and 6 g of 2-methoxyethyl mesylate and 6.9 g of $K_2CO_3$ was refluxed in acetonitril for 20 h. The resulting mixture was filtered and evaporated. The residue was dissolved in methylene chloride and extracted with water containing 1 g of NaOH, then with water and then dried over $Na_2SO_4$, filtered and evaporated. The residue was crystallized from ethyl acetate yielding N-(2-((2-hydroxy-3-(4-(2-methoxyethoxy)phenoxy)propyl)amino)ethyl)-4-morpholinecarboxamide. Melting point 69° C. (base).

EXAMPLE 10

(Method h)

5.7 g of 1-(2-aminoethylamino)-3-(4-(2-methoxyethoxy)phenoxy)propanol-2, 3 g of 4-morpholinecarbonyl chloride, and 10 ml of triethylamine were refluxed in 70 ml of acetonitril for 4 hours. The resulting mixture was evaporated and the residue dissolved in methylene chloride. This solution was washed with water, dried over $Na_2SO_4$, filtered, and concentrated to yield a residue from which N-(2-((2-hydroxy-3-(4-(2-methoxyethoxy)phenoxy)propyl)amino)ethyl)-4-morpholinecarboxamide was crystallized with the aid of ethyl acetate. Melting point 69° C. (base).

EXAMPLE 11

(Method n)

3.3 g of N-(2-((2-hydroxy-3-(4-(2-methoxyethoxy)phenoxy)propyl)amino)ethyl)urea and 2.6 g of the dimesylate of 2-(2-hydroxyethoxy)ethanol were added to a solution of 500 ml of ethanol and 0.5 g of Na. The solution was first stirred at room temperature for 3 h and then refluxed for 24 h and evaporated. The residue was partitioned between water and methylene chloride. The organic layer was dried over $Na_2SO_4$, filtered, and concentrated. From the residue N-(2-((2-hydroxy-3-(4-(2-methoxyethoxy)phenoxy)propyl)amino)ethyl)-4-morpholinecarboxamide was crystallized from ethyl acetate and ether. Melting point 69° C. (base).

EXAMPLE 12

(Method s)

2.8 g of the hydrochloride of 1-amino-3-(4-(2-methoxyethoxy)phenoxy-propanol-2, 1.8 g of N-(2-oxoethyl)-4-morpholinecarboxamide, and 1 g of sodium cyanoborohydride were mixed in 100 ml of ethanol. The mixture was stirred for 24 h at room temperature. Most of the solvent was evaporated and ether was added. The mixture was then extracted with diluted hydrochloric acid. The water layer was made alkaline with ammonia and extracted with methylene chloride. The organic phase was dried over $Na_2SO_4$, filtered, and concentrated. N-(2-((2-hydroxy-3-(4-(2-methoxyethoxy)phenoxy)propyl)amino)ethyl)-4-morpholinecarboxamide was crystallized from the residue with the aid of ethyl acetate. Melting point 69° C. (base).

EXAMPLE 13

(Method u)

4 g of N-(2-((2-oxo-3-(4-(2-methoxyethoxy)phenoxy)propyl)amino)ethyl)-4-morpholinecarboxamide was dissolved in 50 ml of methanol and the solution was cooled to 0° C. on an ice bath. 1 g of $NaBH_4$ was added little by little while stirring first at 0° C. for 1 hour and then at ambient temperature for 0.5 hours. The solution thus obtained was evaporated whereupon 100 ml of $H_2O$ was added. The aqueous phase was extracted 3 times with methylene chloride. The collected methylene chloride phase was dried over $Na_2SO_4$, filtered and concentrated. N-(2-((2-hydroxy-3-(4-(2-methoxyethoxy)phenoxy)propyl)amino)ethyl)-4-morpholinecarboxamide was crystallized from the residue using ethyl acetate. Melting point 69° C. (base).

EXAMPLE 14

(Method q and r)

5.3 g of N-(2-((2-hydroxy-3-(4-(2-(2-methyl-2-propenyloxy)ethoxy)phenoxy)propyl)-(N'-benzyl)amino)ethyl-4-morpholinecarboxamide was dissolved in 150 ml of ethanol. 0.2 g of Pd/C (5%)-catalyst was added and the mixture was hydrogenated until 500 ml of hydrogen had been absorbed. The catalyst was filtered off and the filtrate concentrated. N-(2-((2-hydroxy-3-(4-(2-(2-methylpropoxy)ethoxy)phenoxy)propyl)amino)ethyl)-4-morpholinecarboxamide was obtained from the residue by treating with ethyl acetate. Melting point 95°-96° C. (base).

EXAMPLE 15

Preparation of N-(2-((2-hydroxy-3-(4-(2-(2-methylpropoxy)ethoxy)phenoxy)propyl)amino)ethyl-N'-methyl urea 10.6 g of 3-(4-(2-(2-methylpropoxy)ethoxy)phenoxy)-1,2-epoxypropane and 14 g of N-2-aminoethyl-N'-methyl-urea was refluxed 40 h in isopropanol. The product crystallized when the heating was stopped. Recrystallized from isopropanol. Yield 8 g. M.p. 121° C. (base). The structure was determined using NMR.

EXAMPLE 16

Preparation of N,N-dimethyl-N'-(2-((2-hydroxy-3-(4-(2-(2-methylpropoxy)ethoxy)phenoxy)propyl)amino)ethyl)urea 8 g of 3-(4-(2-(2-methylpropoxy)ethoxy)phenoxy)-1,2-epoxypropane and 14 g of N-2-aminoethyl-N',N'-dimethylurea was warmed (60°-70° C.) in 150 ml of isopropanol over night. The mixture was evaporated and the residue dissolved in ethyl acetate. The ethyl acetate phase was washed with water (twice), fresh water was then added and pH lowered to 5 with hydrochloric acid. Fresh ethyl acetate was then added to the water phase and pH was rised to 9.5. The organic phase was separated off, dried, and evaporated. The residue was recrystallized from a small amount of ethyl acetate. Yield 3 g. M.p. 75° C. (base). The structure was determined using NMR-analysis.

EXAMPLE 17

N-(2-((2-hydroxy-3-(4-(2-(2-propoxy)ethoxy)phenoxy)propyl)amino)ethyl)-N'-methyl-urea was prepared in accordance with example 15. M.p. 105° C. (base).

EXAMPLE 18

N-(2-((2-hydroxy-3-(4-(2-(2-methoxy)ethoxy)phenoxy)propyl)amino)ethyl)-N'-methyl-urea was prepared in accordance with example 15. M.p. 116° C. (base).

EXAMPLE 19

N-(2-((2-hydroxy-3-(4-(2-(2-methylpropoxy)ethoxy)phenoxy)propyl)amino)ethyl)-N'-2-methoxyethyl-urea hydrochloride was prepared in accordance with example 15. M.p. 105° C. (HCl).

EXAMPLE 20

N-(2-((2-hydroxy-3-(4-(2-propoxyethoxy)phenoxy)propyl)amino)ethyl)-4-morpholinecarboxamide was prepared in accordance with example 3. M.p. 88° C. (base).

EXAMPLE 21

N-(2-((2-hydroxy-3-(4-(2-(2,2-dimethylpropoxy)ethoxy)phenoxy)propyl)amino)ethyl)-4-morpholinecarboxamide was prepared in accordance with example 3. The product was however chromatographed on silica. M.p. 90° C. (base).

EXAMPLE 22

N-(2-((2-hydroxy-3-(2-bromo-4-(2-ethoxyethoxy)phenoxy)propyl)amino)ethyl)-4-morpholinecarboxamide was prepared in accordance with example 3. M.p. 98° C. (base).

EXAMPLE 23

2-((2-hydroxy-3-(4-(2-propoxyethoxy)phenoxy)propyl)amino)ethyl urea was prepared in accordance with example 3. M.p. 115° C. (base).

EXAMPLE 24

N,N-dimethyl-N'-(2-((2-hydroxy-3-(4-(2-cyclopropylmethoxyethoxy)phenoxy)propyl)amino)ethyl)urea was prepared in accordance with example 16. M.p. 86° C. (base).

EXAMPLE 25

N-(2-((2-hydroxy-3-(4-(2-(2-methylpropoxy)ethoxy)phenoxy)propyl)amino)ethyl)-N'-2-methoxyethyl-N'-methyl urea was prepared in accordance with example 16. M.p. 60°-63° C. (base).

EXAMPLE 26

N,N-diethyl-N'-(2-((2-hydroxy-3-(4-(2-methoxyethoxy)phenoxy)propyl)amino)ethyl)urea was prepared in accordance with example 16. M.p. 104° C. (½ H2SO4).

EXAMPLE 27

N,N-di-(2-methoxyethyl)-N'-(2-((2-hydroxy-3-(4-(2-methoxyethoxy)phenoxy)propyl)amino)ethyl)urea was prepared in accordance with example 16.

EXAMPLE 27A 20.0 g N-[2-[[2-hydroxy-3-[4-(2-methoxyothoxy)phenoxy]propyl]amino]ethyl]-4-morpholinecarboxamide were mixed with 6.4 ml benzyl chloride, 8.3 g K2CO3 and 200 ml CH3CN and refluxed for 6 hours. The mixture was filtered while hot and evaporated in vacuo. Yield 25.4 g of N-[2-[[2-hydroxy-3-[4-(2-methoxyethoxy)phenoxy]propyl]benzylamino]ethyl]-4-morpholinecarboxamide as a yellow oil. The structure below was confirmed using NMR.

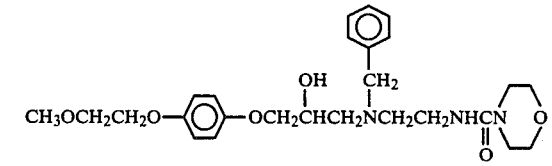

7.5 g of the product was dissolved in 15 ml pyridine and 1.96 ml benzoyl chloride was added. The mixture was left for 2 days at ambient temperature and evaporated in vacuo. 8.1 g residue was purified on a Silica-gel column. Yield 4.2 g oil. The structure below was confirmed using MS and NMR.

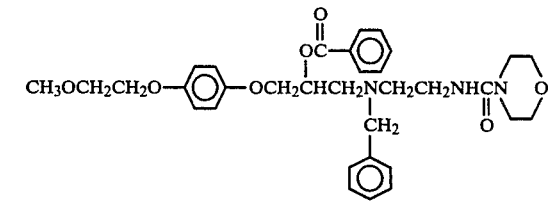

4.2 g of the product obtained was dissolved in 95% ethanol and treated with active carbon. The ethanol solution was filtered and hydrogenated, using a 5% Pd on carbon as catalyst, at atmospheric pressure to split off the benzyl group. The solution was filtered, evaporated in vacuo and crystallized from ethyl acetate. Yield 2.0 g of N-[2-[[2-benzoyloxy-3-[4-(2-methoxyothoxy)phenoxy]propyl]amino]ethyl]-4-morpholinecarboxamide. Melting point 133°-134° C. Structure according to formula LX above was confirmed using $^{13}C$- and H-NMR.

EXAMPLE 28

An injection solution was prepared by dissolving N-(2-((2-hydroxy-3-(4-(2-methoxyethoxy)phenoxy)propyl)amino)ethyl)-4-morpholinecarboxamide hydrochloride (1 g), sodium chloride (0.8 g) and ascorbic acid (0.1 g) in a sufficient ammount of distilled water to give 100 ml of solution. This solution, which contains 10 mg of active substance per each ml, was used in filling ampoules, which were sterilized.

EXAMPLE 29

A sirup containing 2% (weight per volume) of active substance was prepared from the following ingredients:

| | |
|---|---|
| N—[2-[[2-hydroxy-3-[4-[2-methoxyethoxy]phenoxy]propyl]-amino]ethyl]-4-morpholinecarboxamide.HCl | 2.0 g |
| Saccharine | 0.6 g |
| Sugar | 30.0 g |
| Glycerine | 5.0 g |
| Flavouring agent | 0.1 g |
| Ethanol 96% | 10.0 ml |
| Distilled water ad | 100.0 ml |

Sugar, saccharine and the ammonium salt were dissolved in 60 g of warm water. After cooling glycerine and a solution of flavouring agents dissolved in ethanol were added. To the mixture water was then added to 100 ml.

EXAMPLE 30

N-(2-((2-hydroxy-3-(4-(2-methoxyethoxy)phenoxy)propyl)amino)ethyl)-4-morpholinecarboxamide hydrochloride (250 g) was mixed with lactose (175.8 g), potato starch (169.7 g) and colloidal silicic acid (32 g). The mixture was moistened with 10% solution of gelatine and was granulated through a 12-mesh sieve. After drying potato starch (160 g), talc (50 g) and magnesium stearate (5 g) were admixed and the mixture thus obtained was pressed into tablets (10,000) which contain 25 mg of substance. The tablets are sold on the market provided with a breaking score to give another dose than 25 mg or to give multiples thereof when broken.

EXAMPLE 31

Granules were prepared from N-(2-((2-hydroxy-3-(4-(2-methoxyethoxy)phenoxy)propyl)amino)ethyl)-4-morpholinecarboxamide.hydrochloride (250 g), lactose (175.9 g) and an alcoholic solution of polyvinylpyrrolidone (25 g). After the drying step the granules were mixed with talc (25 g), potato starch (40 g) and magnesium stearate (2.50 g) and was pressed into 10,000 tablets being biconvex. These tablets are primarily coated with a 10% alcoholic solution of shellac and thereupon with an aqueous solution containing saccharose (45%), gum arabicum (5%), gelatine (4%) and dyestuff (0.2%). Talc and powder sugar were used for powdering after the first five coatings. The coating was then coated with a 66% sugar sirup and polished with a 10% carnauba wax solution in carbon tetrachloride.

BIOLOGICAL EFFECTS

Experiment A

The effects of compounds of the invention on cardiac and vascular $\beta$-adrenoceptors were evaluated using the following experimental procedure.

Cats of both sexes were pretreated with reserpine (5 mg/kg) which was injected i.p. 16 hours before sodium pentobarbital (30 mg/kg) anaesthesia. Artificial respiration was supplied via a tracheal cannula and both vegal nerves were cut. Heart rate was recorded from the blood pressure oscillations. The femoral artery of one hind leg was cannulated in both directions and blood from the proximal part was pumped at a constant flow rate into the distal part of the artery. Alterations in the perfusion pressure indicated changes in the peripheral vascular resistance.

The i.v. dose of isoprenaline which elevated the heart rate by approximately 80 percent of the maximal effect of isoprenaline was determined. This dose of isoprenaline induced a vasodilatation in the hind leg which was also about 80 percent of the maximal response. After these control responses had been obtained the experiments were run in cycles of 30 min. Each cycle started with an intravenous infusion of either of the test compounds for 10 min. Another 10 min after the drug infusion was stopped the control of isoprenaline was given.

For each dose of the test compound the peak reduction of the isoprenaline heart rate (HR) and perfusion pressure (PP) responses were expressed as percent blockage according to the formula:

$$100 \times \frac{\text{Reduction of the isoprenaline induced response (HR: beats per min; PP: mm Hg)}}{\text{Control isoprenaline response (HR: beats per min; PP: mm Hg)}}$$

The lowest dose of test compound was 0.05 $\mu$mol/kg. The dose was then increased by a factor of four for each cycle. The percent blockade of the heart rate and perfusion pressure responses to isoprenaline was calculated and plotted versus the cumulative doses of the test compounds on a logarithmic scale. The ED$_{50}$-values calculated from these curves were taken to indicate the blocking potencies of the compounds.

Experiment B

The intrinsic sympathomimetic activity of the test compounds was evaluated in reserpine pretreated (5 mg/kg i.p. 16 hours before sacrifice), anaesthetized (sodium pentobarbital 30 mg/kg) and vagotomized cats of either sex. Heart rate was recorded from the blood pressure oscillations via a carotid artery catheter.

After a maximal heart rate response to isoprenaline was established the test compounds were slowly injected intravenously (during 2 min) every 12 min in stepwise increasing doses. The heart rate was recorded 5 min after administration of each dose of test compound until no further increase in heart rate was obtained at additional administration. Finally the maximal response to isoprenaline was reestablished and the intrinsic sympathomimetic activity of the test compounds were expressed as percent of the maximal effect of isoprenaline according to the formula:

$$100 \times \frac{\text{maximal effect of test compound (beats per minute)}}{\text{postdrug maximal effect of isoprenaline (beats per minute)}}$$

The effects of the test compounds evaluated according to experiments A and B were as follows:

The $\beta_1$-adrenoceptor blocking potencies (HR) of the compounds tested, as determined in the anaesthetized cat, expressed as ED$_{50}$, were in the range 0.03–1.2

μmol/kg while the $\beta_2$-adrenoceptor blocking potencies (PP) were in the range 12->50 μmol/kg and the selectivity ratios ($ED_{50}PP/ED_{50}HR$) were in the range about 50->1000. The compound of Example 5 and in particular the compound of Example 3 displayed a high, very strongly $\beta_1$-selective potency.

The intrinsic sympathomimetic activity recorded as positive chronotropic effect ranged between about 15 and 35 typically between 25 and 35 percent of the maximal heart rate elevation.

The results indicate that the compounds of the invention are $\beta$-adrenoceptor blocking compounds with a strong selectivity in blocking $\beta_1$-receptors and a degree of intrinsic sympathomimetic activity on cardiac $\beta$-adrenoreceptor desirable in treatment of certain cardiac disorders.

We claim:

1. A compound of the formula

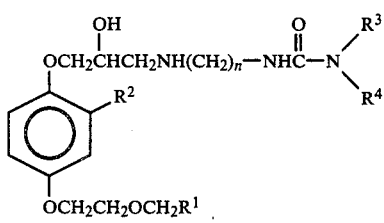

or a pharmaceutically acceptable salt thereof, in which formula
   $R^1$ is H, a straight or branched alkyl group containing 1–5 carbon atoms, a cycloalkyl group containing 3–6 carbon atoms, or a cycloalkylalkyl group containing 4–6 carbon atoms;
   $R^2$ is H;
   n is 2, 3, or 4; and
   $R^3$ and $R^4$ together with the adjacent nitrogen atom form a morpholino group.

2. A compound according to claim 1, or a pharmaceutically acceptable salt thereof, wherein $R^1$ is H, $C_2H_5$, isopropyl, or cyclopropyl, and wherein n, $R^2$, $R^3$ and $R^4$ are as defined in claim 1.

3. A compound according to claim 1, or a pharmaceutically acceptable salt thereof, wherein n is 2, and wherein $R^1$, $R^2$, $R^3$ and $R^4$ are as defined in claim 1.

4. The compound according to claim 1 N-(2-((2-hydroxy-3-(4-(2-methoxyethoxy)phenoxy)propyl)amino)ethyl)-4-morpholinecarboxamide or a pharmaceutically acceptable salt thereof.

5. The compound according to claim 1 N-(2-((2-hydroxy-3-(4-(2-cyclopropylmethoxyethoxy)phenoxy)propyl)amino)ethyl)-4-morpholinecarboxamide or a pharmaceutically acceptable salt thereof.

6. The compound according to claim 1 N-(2-((2-hydroxy-3-(4-(2-(2-methylpropoxy)ethoxy)phenoxy)propyl)amino)ethyl)-4-morpholinecarboxamide or a pharmaceutically acceptable salt thereof.

7. The compound according to claim 1 N-(2-((2-hydroxy-3-(4-(2-propoxyethoxy)phenoxy)propyl)amino)ethyl)-4-morpholinecarboxamide or a pharmaceutically acceptable salt thereof.

8. A compound according to claim 1 in the form of a substantially pure optical isomer.

9. A pharmaceutical preparation comprising an amount of compound effective to block the cardiac adrenergic beta-receptor, which compound has the formula

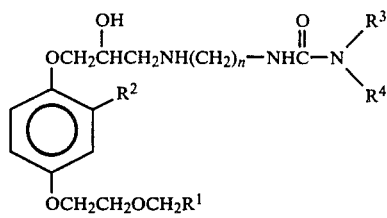

or a pharmaceutically acceptable salt thereof, wherein
   $R^1$ is a straight or branched alkyl group containing 1–5 carbon atoms, or a cycloalkylalkyl group containing 4–6 carbon atoms;
   $R^2$ is H
   n is 2, 3, or 4; and
   $R^3$ and $R^4$ together with adjacent nitrogen atom form a morpholino group; and
a pharmaceutically acceptable carrier therefor.

10. A pharmaceutical preparation according to claim 8, wherein $R^1$ is $CH_3$.

11. A pharmaceutical preparation according to claim 8, wherein $R^1$ is isopropyl.

12. A pharmaceutical preparation according to claim 8, wherein $R^1$ is cyclopropyl.

13. A method for blocking the cardial beta-receptors in mammals including man, comprising administering to a host in need of such blockage a compound of the formula

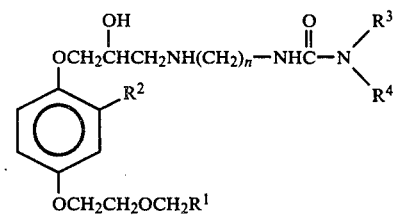

or a pharmaceutically acceptable salt thereof, in which formula
   $R^1$ is H, a straight or branched alkyl group containing 1–5 carbon atoms, a cycloalkyl group containing 3–6 carbon atoms, or a cycloalkylalkyl group containing 4–6 carbon atoms;
   $R^2$ is H
   n is 2, 3, or 4; and
   $R^3$ and $R^4$ together with the adjacent nitrogen atom form a morpholino group.

14. A method according to claim 13 comprising administering the compound N-(2-((2-hydroxy-3-(4-(2-methoxyethoxy)phenoxy)propyl)amino)ethyl)-4-morpholine-carboxamide or a pharmaceutically acceptable salt thereof.

15. A method according to claim 13 comprising administering the compound N-(2-((2-hydroxy-3-(4-(2-cyclopropylmethoxyethoxy)phenoxy)propyl)amino)ethyl)-4-moropholinecarboxamide or a pharmaceutically acceptable salt thereof.

16. A method according to claim 13 comprising administering the compound N-(2-((2-hydroxy-3-(4-(2-(2-methylpropoxy)ethoxy)phenoxy)propyl)amino)ethyl)-4-moropholinecarboxamide or a pharmaceutically acceptable salt thereof.

17. A method according to claim 13 comprising administering the compound N-(2-((2-hydroxy-3-(4-(2- propoxyethoxy)phenoxy)propyl)amino)ethyl)-4-morpholinecarboxamide or a pharmaceutically acceptable salt thereof.

18. A method for treatment of cardiac disorders in mammals including man, characterized in administering to a host in need of such treatment a compound of the formula

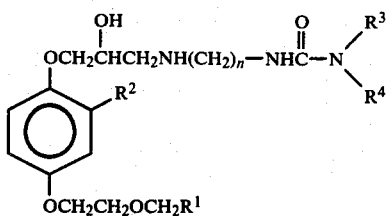

or a pharmaceutically acceptable salt thereof, in which formula
$R^1$ is H, a straight or branched alkyl group containing 1-5 carbon atoms, a cycloalkyl group containing 3-6 carbon atoms, or a cycloalkylalkyl group containing 4-6 carbon atoms;
$R^2$
n is 2, 3, or 4; and
$R^3$ and $R^4$ together with the adjacent nitrogen atom form a morpholino group.